United States Patent
Eismann et al.

(10) Patent No.: US 8,633,429 B2
(45) Date of Patent: Jan. 21, 2014

(54) IMAGE PICK-UP MODULE WITH CONTACT POINT CIRCUIT CONNECTION

(75) Inventors: Dirk Eismann, Ligerz (CH); Martin Klumpp, Tuttlingen (DE); Peter Schwarz, Tuttlingen-Nendingen (DE)

(73) Assignee: Karl Storz GmbH & Co. KG (DE)

( * ) Notice: Subject to any disclaimer, the term of this patent is extended or adjusted under 35 U.S.C. 154(b) by 120 days.

(21) Appl. No.: 13/246,271

(22) Filed: Sep. 27, 2011

(65) Prior Publication Data

US 2012/0104230 A1     May 3, 2012

(30) Foreign Application Priority Data

Sep. 27, 2010   (DE) .................. 10 2010 047 288

(51) Int. Cl.
*H01L 27/00*     (2006.01)
(52) U.S. Cl.
USPC .................................................. 250/208.1
(58) Field of Classification Search
USPC ........... 250/208.1; 348/65, 294; 600/109, 110
See application file for complete search history.

(56) References Cited

U.S. PATENT DOCUMENTS

| | | | |
|---|---|---|---|
| 5,021,888 A | 6/1991 | Kondou et al. | |
| 5,754,313 A | 5/1998 | Pelchy et al. | |
| 5,879,285 A | 3/1999 | Ishii | |
| 6,494,739 B1 | 12/2002 | Vivenzio et al. | |
| 2002/0080233 A1 | 6/2002 | Irion et al. | |
| 2004/0263680 A1 | 12/2004 | Sonnenschein et al. | |
| 2006/0109368 A1 | 5/2006 | Ayrenschmalz | |
| 2009/0021618 A1 | 1/2009 | Schwarz et al. | |
| 2010/0041268 A1 | 2/2010 | Okada et al. | |

FOREIGN PATENT DOCUMENTS

| | | |
|---|---|---|
| EP | 1659780 A1 | 5/2006 |
| EP | 2018043 A1 | 1/2009 |
| WO | 0072744 A2 | 12/2000 |

OTHER PUBLICATIONS

European Search Report; Application No. EP 11 18 2213; Issued: Nov. 22, 2011; 8 pages.

*Primary Examiner* — Thanh Luu
*Assistant Examiner* — Renee Naphas
(74) *Attorney, Agent, or Firm* — St. Onge Steward Johnston & Reens LLC (57) ABSTRACT

An image pick-up module and method for producing an image pick-up module. An image pick-up module, particularly for installation in an endoscope, the image pick-up module having an electronic image sensor, a first circuit board, a second circuit board and a cable.

14 Claims, 4 Drawing Sheets

IMAGE PICK-UP MODULE WITH CONTACT POINT CIRCUIT CONNECTION

CROSS-REFERENCE TO RELATED APPLICATION

This application claims priority from German patent application 10 2010 047 288.3, filed on Sep. 27, 2010. The entire content of these priority application is incorporated herein by reference.

BACKGROUND OF THE INVENTION

The invention generally relates to image pick-up modules, particularly for an installation in an endoscope. More specifically, the invention relates to an image pick-up module, comprising an electronic image sensor, a first circuit board, a second circuit board, and a cable.

The invention further relates to a method for producing an image pick-up module.

An electronic image pick-up module according to the invention is preferably used in an endoscope, particularly in a flexible endoscope, the image pick-up module being arranged in the distal end of the endoscope shaft. Such an endoscope or video endoscope, respectively, is described, for example, in U.S. Pat. No. 5,754,313. Other illustrative uses of the image pick-up module according to the invention are the installation in a microscope, a medical miniature camera, an exoscope etc.

An image pick-up module generally comprises an electronic image sensor which converts light incident on it into electrical signals. Generally, such electronic image sensors are constructed in CCD or CMOS technology.

At present, miniaturized image sensors can be obtained among which those are preferred which are produced in TAB (Tape Automated Bonding) technology. Such image sensors have contact fingers arranged in at least one row, usually in two rows on opposite narrow sides of the image sensor, which extend approximately perpendicularly to the light receiving side of the image sensor away from the latter in the image pick-up module.

The use of an image pick-up module for an endoscope in which the image pick-up module is installed into the distal tip of the endoscope shaft necessitates a miniaturized constructional size of the image pick-up module. However, the production of a miniaturized image pick-up module is afflicted with technical problems, especially with regard to the assembling of the arrangement of the image sensor, circuit board and cable.

In the prior art, various constructions of image pick-up modules have been described which, however, do not satisfactorily solve the technical problems in the assembling of the components of the image pick-up module.

In the document EP 2 018 043 A1, an image pick-up module is shown in its FIGS. 4a and 4b which has two circuit boards which are arranged behind one another in a direction perpendicular to the light-receiving surface of the image sensor. The first circuit board, seen from the image sensor, is here equipped with electronic or electrical components. The second circuit board which is arranged on the side of the first circuit board facing away from the image sensor is used for terminating the multi-wire cable. For this purpose, the second circuit board has a plurality of through holes into which the individual wires of the cable are inserted. The ends of the wires are here located approximately on the inner surface of the second circuit board which is constructed to be U-shaped overall. In the assembled state, the contact fingers of the image sensor encompass the second circuit board on its rear so that the contact fingers electrically conductively contact the second circuit board. Due to the U-shaped construction of the second circuit board, the second circuit board is in electrically conductive contact with the first circuit board via leads which, however, is difficult with a miniaturized construction of the two circuit boards and, in particular, is not suitable for an automated assembly by means of a robot.

In the document mentioned above, in a further illustrative embodiment, an image pick-up module which only has a single circuit board is shown in FIGS. 7a to 7c there. This circuit board has through holes through which the wires of the cable are passed, the wires being brought out of the surface of the circuit board facing the image sensor with their wire jackets and being bent over in order to bring the ends of the wire cores, after having been stripped, into electrically conductive contact with the circuit board. In this embodiment, the problem is that the ends of the wires must be stripped so that the wire cores can be soldered onto the surface of the circuit board facing the image sensor. For this reason, this image pick-up module is also not suitable for an automated assembly by means of a robot.

From the document EP 1 659 780 A1, a further image pick-up module is known which has a single circuit board which is both equipped with electrical or electronic components and used for terminating the multi-wire cable. The circuit board is constructed to be U-shaped or with a notch in the surface facing the image sensor. In this image pick-up module, the at least one electronic component is in electrically conductive contact with the circuit board by means of conductor leads which are run three-dimensionally in the space created by the U-shaped construction or by the notch, respectively. Such "air wiring" of the components of the image pick-up module is also not suitable for automatic production, especially not for an automatic production by means of a robot. The wires of the cable are contacted on the rear of the circuit board in this known image pick-up module.

In the document WO 00/72744 A2, an image pick-up module is described, the circuit board of which is formed from a one-piece plate foldable along flexible connecting sections, which plate can be folded to form a cube-shaped, cross-sectionally essentially U-shaped body. The circuit board body has in its folded state two sections essentially extending transversely to the image sensor and spaced apart, and a third space which extends essentially in parallel with the image sensor. Such an image pick-up module, too, is not suitable for automatic assembly of the individual components of the image pick-up module.

From document U.S. Pat. No. 6,494,739 B1, an image pick-up module is known which has a connecting piece with which the image sensor and a control circuit board are connected and which is used for electrically contacting a multi-wire cable. The wires of the multi-wire cable are fixed on the connecting piece in lateral indentations in the form of grooves which are metallized, and put in contact with the metallizations. The control circuit board with the image sensor is also in electrical contact with the connecting piece via metallizations. In a further illustrative embodiment in this document, the connecting piece is constructed of two plane-parallel plates, the plate facing away from the image sensor being used for electrically contacting the shields of the individual wires of the multi-wire cable and the plate facing the image sensor being used for contacting the signal conductors of the wires of the multi-wire cable. Here, too, there are on the two plates laterally, that is to say on their narrow sides, groove-like indentations for accommodating the shields or the conductors, respectively. The connecting piece does not have any through holes for passing through the wires of the multi-wire cable.

A further image pick-up module is known from the document US 2004/0263680 A1. In one embodiment described there, two plane-parallel circuit board parts are present which are spaced apart comparatively far from one another in the longitudinal direction of the image pick-up module. The wires of a multi-wire cable are partially in electrical contact with the underside of the circuit board part facing away from the image sensor, are partially passed through holes in this circuit board part and are in electrical contact with the latter as air wiring, bridging the distance from the circuit hoard part facing the image sensor.

Apart from the lacking suitability of the known image pick-up modules for automated assembly of the components of the image pick-up module, the known image pick-up modules have the further disadvantage that the image pick-up modules can only be subjected to a functional test when they are completely assembled, i.e. when the image sensor is also in electrically conductive contact with the circuit board or circuit boards. If, however, the contact arrangements and wiring arrangements of the circuit board or of the circuit boards are faulty, the entire image pick-up module including the expensive image sensor is unusable. In the known image pick-up modules, there is thus an undesirably high rejection rate of image sensors operating correctly per se.

In the known image pick-up modules, the wires of the multi-wire cable must be stripped individually before they are soldered onto the at least one circuit board, and cut to the correct length. In this context, the individual wires must end as shortly behind the cable root as possible, so that the constructional length of the entire module is as small as possible. This requirement complicates the stripping and trimming of the cables extremely and also renders this process very time-consuming.

SUMMARY OF THE INVENTION

The invention is based on the object of developing an image pick-up module to the extent that it can be assembled in a simple manner and that, in particular, it is suitable for automatic assembly, for example by means of a robot.

The invention is also based on the object of specifying a method for producing an image pick-up module which can be performed in an automated manner.

According to an aspect of the invention, an image pick-up module is provided, comprising: an electronic image sensor which has a plurality of contact fingers which are arranged in at least one row, the electronic image sensor having a light-receiving surface, a first circuit board being arranged in parallel with the light-receiving surface of the image sensor, the first circuit board having at least one electronic or electrical component, a first surface facing away from the image sensor, a second circuit board arranged in parallel with the first circuit board on a side of the first circuit board facing away from the image sensor, the second circuit board having a second surface facing away from the first circuit board, and a third surface facing the first circuit board, the third surface being essentially level overall, a plurality of holes distributed two-dimensionally over the second circuit board between edges of the second circuit board, the holes going through from the second surface to the third surface of the second circuit board, the holes being distributed according to a first distribution, a cable having a plurality of wires being connected to the second circuit hoard and leading away from the second surface of the second circuit board, the wires having ends introduced into the holes of the second circuit board, and the ends of the wires being located approximately on the third surface of the second circuit board, the first circuit board has on the first surface facing the second circuit board a plurality of punctiform first electrical contact points distributed according to a second distribution which corresponds to the first distribution of the ends of the wires on the third surface of the second circuit board, the first circuit board being in electrically conductive contact with the ends of the wires via the first electrical contact points.

The image pick-up module according to the invention is based on a design in which, instead of a single circuit board, there are two circuit boards, the first circuit board of which is equipped with at least one electronic or electrical component, whilst the second circuit board, which is arranged on the side of the first circuit board facing away from the image sensor, is used for terminating the multi-wire cable. In this arrangement, both circuit boards are arranged in parallel with the light-receiving side of the image sensor. In principle, both circuit boards can have the form of a cube, the main surfaces of which are arranged in parallel with the light-receiving side of the image sensor and the surfaces of which perpendicular to these surfaces form narrow sides of the respective circuit board.

In the second circuit board, there are a plurality of holes which are going through between the two surfaces of the second circuit board extending in parallel with the light-receiving side of the image sensor. Into these holes, the wires of the multi-wire cable are inserted so that ends of the wires are located approximately on the surface of the second circuit board facing the first circuit board.

In distinction from the construction of the known image pick-up module which also has two circuit boards, the second circuit board of the image pick-up module according to the invention does not have, on its surface facing the first circuit board, a U-profile or a notch, but the surface of the second circuit board facing the first circuit board is essentially level overall. This provides the advantage that during the termination of the multi-wire cable at the second circuit board, the individual wires can be passed through the holes in the second circuit board with their wire jackets until the ends of the wires protrude on the surface of the second circuit board facing away from the cable root. Subsequently, it is then possible in a simple manner to trim the wires flush with this surface of the second circuit board by cutting along this surface perpendicularly to the wires. This process can be performed automatically with a corresponding device. During this process, stripping of the wire jackets is advantageously omitted because the wire cores are bluntly exposed at their ends by the cutting.

In the image pick-up module according to the invention, the first circuit board is also provided on its surface facing the second circuit board with a plurality of punctiform first electrical contact points, the surface distribution of which corresponds to the surface distribution of the ends of the wires on the surface of the second circuit board. The first circuit board is directly brought into electrically conductive contact with the wires via these punctiform electrical contact points. This also contributes to a simplified assembly, and one that is particularly suitable for automation, of the second circuit board with the first circuit board. This is because the first circuit board only needs to be placed onto the second circuit board in order to produce the electrical contact of the first circuit board with the second circuit board. Air wiring as in the case of the known image pick-up modules, which is riot suitable for automated assembly, is thus advantageously omitted.

"Punctiform electrical contact points" is here understood to mean that the first contact points are formed in the form of minute islands on the surface of the first circuit board facing the second circuit board.

The first contact points are preferably so flat that they are not, or not significantly, elevated with respect to the surface of the first circuit board on which they are present. As a result, it is then possible to arrange the first circuit board and the second circuit board very closely to one another with a small gap between them in the sense of an axially short way of construction.

The image pick-up module according to the invention can thus be produced by means of an automated method at least with respect to the termination of the multi-wire cable and the contacting of the first circuit board with the second circuit board.

In addition, the image pick-up module according to the invention is advantageously constructed to be very short in the axial direction, i.e. perpendicularly to the light-receiving surface of the image sensor.

In a preferred embodiment, the first circuit board has, on at least one narrow side, a plurality of second contact points, the contact fingers of the image sensor being in electrically conductive contact at the second contact points.

in this context, it is advantageous that the contact fingers of the image sensor, which are sensitive to mechanical loading, need to be bent over only once after removal of the image sensor from its packaging, namely from a direction in parallel with the light-receiving side of the image sensor into a direction perpendicular to this. In the image pick-up module known from EP 2 018 043 A1 (FIGS. 4a, 4b), the contact fingers are additionally bent over again at right angles at their extreme end, which can lead to the contact fingers breaking off. The further advantage of the measure mentioned above consists in that before the image sensor is attached to the arrangement of the first and second circuit board, a functional test of all conductive connections can be carried out at the second contact points without the image sensor first having to be brought into electrical contact with the arrangement of the first circuit board and second circuit board for this purpose.

In connection with the aforementioned measure, the second contact points are preferably constructed as conductive indentations, extending in the direction from the surface facing the image sensor to the opposite surface of the first circuit board, on the at least one narrow side.

In this context, it is advantageous that the contact fingers can be brought into contact with the first circuit board in a simple manner by means of conductive adhesive or solder applied into the conductive indentations.

The conductive indentations are preferably constructed as essentially half-cut-open cylinders.

In this context, it is advantageous that the second contact points on the first circuit board can also be produced in a simple manner. Thus, for example, continuous holes can be introduced in one or two rows on opposite edge areas of the first circuit board into the first circuit board which initially is manufactured with an excessive dimension, and by cutting off above the edges of the circuit board approximately centrally through the holes, the half cylinders are then produced which only have to be metallized when the metallization has not already been entered into the holes.

In a further preferred embodiment, the first circuit board is in contact with and connected to the wires at the first contact points by means of conductive joining points.

This measure has the advantage that the first circuit board is not only electrically conductively brought into contact with the second circuit board via the first contact points, but a mechanical connection is also established via the joining points, for example adhesive or solder points between the two circuit boards without further measures having to be taken for a mechanical connection of the two circuit boards with one another. In addition, the joining points can be applied either on the exposed ends of the wires or conversely on the first contact points of the first circuit board automated by means of a robot. After the joining points have been applied, the first circuit board then only needs to be placed onto the second circuit board, which can also be performed by means of a robot in an automated manner.

In an alternative embodiment, between the first circuit board and the second circuit board in the area of the first contact points, a two-dimensional element is arranged which is manufactured from an insulating compressible material which is interspersed with conductive particles, the two-dimensional element being locally compressed at the first contact points in order to bring the first circuit board electrically conductively into contact with the wires.

A so-called conductive rubber is such a two-dimensional element which can be used here. The conductive rubber has rubber as carrier material which is interspersed by conductive particles. The conductive particles, for example carbon or soot particles, come into contact with one another by compressing the rubber and thus in each case generate a conductor path between the respective individual wire and the associated first contact point of the first circuit board. However, in the directions in parallel with the plane of the two dimensional element, the latter remains completely insulating, as a result of which only the associated wire and the first contact point are electrically conductively brought into contact with one another and no short-circuit paths are produced.

In a further preferred embodiment, on the surface, facing the second circuit board, of the first circuit board, spacers are present which define a narrow gap between the surfaces, facing one another, of the first circuit board and of the second circuit board.

This measure is advantageous especially in conjunction with the aforementioned measure, namely when the two circuit boards are brought into contact with one another and connected by means of joining points. By providing spacers between the two circuit boards, a defined joining gap, which is reproducible from image pick-up module to image pick-up module, is always created. In particular, it is avoided that when the first circuit board is placed onto the second circuit board, the joining points are pressed together to such an extent that they become fused together. The spacers can be formed at the first contact points. The spacers can be formed, for example, in the form of so-called ball bonds on the first circuit board. Such "ball bonds" can also be applied to the first circuit board by means of a robot in an automated manner.

In a further preferred embodiment, the wires are fixed in the holes of the second circuit board by means of adhesive.

This measure has the advantage, on the one hand, that a tension relief is created for the cable because the individual wires are mechanically fixed in the holes by the adhesive. On the other hand, this measure has the advantage during the assembly that the wires, after being introduced into the holes, can initially be fixed by means of the adhesive and the above-mentioned cutting along the surface of the second circuit board occurs perpendicularly to the wires thereafter so that during the cutting, the wires are positionally fixed in the holes and the situation can thus not occur in which individual wires can be pulled out of the holes or pulled back into the holes during the cutting.

In a further preferred embodiment, the ends of the wires with their wire cores and their wire jackets end approximately flush with the edges of the holes on the surface facing the first circuit board, of the second circuit board.

In this arrangement, it is advantageous that the position of the ends of the wires is always well defined for all wires, as a result of which, when the first circuit board comes into contact with the second circuit board, it is always ensured that the first contact points are reliably electrically conductively connected to the associated wires.

In a further preferred embodiment, the image sensor is spaced apart from the first circuit board, the space between the image sensor and the circuit board being filled with a casting compound.

Using a curing casting compound in image pick-up modules is known per se. In the image pick-up module according to the invention, however, using the casting compound not only has the advantage of protection of the electrical or electronic components on the first circuit board, but also facilitates the assembly of the image sensor with the arrangement from the first and second circuit board. This is because the casting compound can be applied with a predetermined thickness on the surface of the first circuit board before the image sensor is attached to the first circuit board so that, after the casting compound has cured, the image sensor already has the predetermined distance from the surface of the first circuit board by being set onto the casting compound and the contact fingers are then also arranged at the correct length with respect to the second contact points.

In a further preferred embodiment, the at least one electronically electrical component is arranged on the surface of the first circuit board facing the image sensor.

The arrangement of the at least one electronic or electrical component on the surface of the first circuit board facing the image sensor has the advantage that the first circuit board and the second circuit board can be brought into electrical contact with one another and connected to one another with a very small gap space.

According to another aspect of the invention, a method for producing an image pick-up module is provided, comprising: providing an electronic image sensor which having a plurality of contact fingers arranged in at least one row, providing a first circuit board having a first surface and at least one electronic or electrical component, the first circuit board further having a plurality of punctiform first electrical contact points on the first surface, the first contact points being two-dimensionally distributed according to a first distribution, providing a second circuit board having a second surface being essentially level overall and, further, having a plurality of through holes two-dimensionally distributed over the second circuit board between edges of the second circuit board according to a second distribution corresponding to the first distribution, providing a cable having a plurality of wires having ends, introducing the ends of the wires of the cable into the holes of the second circuit board, arranging the ends of the wires approximately in the area of the second surface of the second circuit board, bringing the first contact points of the first circuit board electrically conductively into contact with the ends of the wires.

As already described above with reference to the image pick-up module according to the invention, the aforementioned method according to the invention can be performed especially in an automated manner, especially by means of a robot.

The wires of the cable are preferably introduced into the holes with their wire jackets until the wires with their wire jackets protrude from the holes, the wires being fixed in the holes by means of adhesive and cutting being effected along the surface of the second circuit board perpendicularly to and through the wires, so that the ends of the wires end approximately flush with edges of the holes on the surface of the second circuit board.

As already mentioned above, the stripping of the wires for exposing the wire cores for the later contacting with the first contact points of the first circuit board is dispensed with by this measure. This is because, due to the cutting perpendicularly to and through the wires, the wire cores are exposed bluntly at the end face, i.e. visibly and contactably.

Conductive joining points are preferably applied to the ends of the wires or onto the first contact points, the first contact points of the first circuit board being placed onto the joining points in order to bring the first circuit board into contact with the wires.

In the aforementioned step, it is not only an electrically conductive contacting of the first circuit board with the second circuit board which takes place but also a mechanical connecting or fixing of the two circuit boards to one another. The aforementioned step can be performed, in particular, in an automated manner by means of a robot.

As an alternative to the aforementioned procedure, on the second circuit board in the area of the wires, a two-dimensional element is arranged which is manufactured from an insulating compressible material which is partially interspersed with conductive particles, the first circuit board being pressed onto the two-dimensional element and fixed on the second circuit board.

As already mentioned above, the two-dimensional element can be a conductive rubber which is interspersed, for example, with carbon or soot particles. In this arrangement, the first circuit board can be fixed to the second circuit board, for example by means of an adhesive which, for example, is only applied to the corners of the first and second circuit board, the two-dimensional element then not being present or at least cut back at these points of adhesion so that the first circuit board and the second circuit board can be fixed to one another by applying pressure on the two-dimensional element.

Furthermore, a casting compound is preferably applied to the first circuit board, the image sensor being placed onto the casting compound and the contact fingers of the image sensor being brought into contact with the first circuit board at second contact points which are arranged on a narrow side of the first circuit board.

Furthermore, before the casting compound is applied and before the image sensor is placed at the second contact points, the functionality of the conductive connections of the first and second circuit board is preferably tested.

The method according to the invention creates not only the possibility of performing the assembly of the image pick-up module in an automated manner by means of a robot, but the method according to the invention and also the image pick-up module according to the invention have the advantage that the functional test for all conductive connections of the first and second circuit board can be performed before the image sensor is attached so that faulty circuit board arrangements can be eliminated and thus there is no waste of expensive image sensors, because these do not need to be attached to the circuit boards for the functional test.

Other advantages and features will become apparent from the subsequent description and the attached drawing.

Naturally, the aforementioned features and those still to be explained in the description which follows can be used not only in the combination specified in each case but also in other combinations or by themselves without departing from the scope of the present invention.

BRIEF DESCRIPTION OF THE DRAWINGS

In the description which follows, an illustrative embodiment of an image pick-up module according to the invention and of a method according to the invention, for producing it, will be described with reference to the attached drawing, in which.

DESCRIPTION OF PREFERRED EMBODIMENTS

Figure 1:
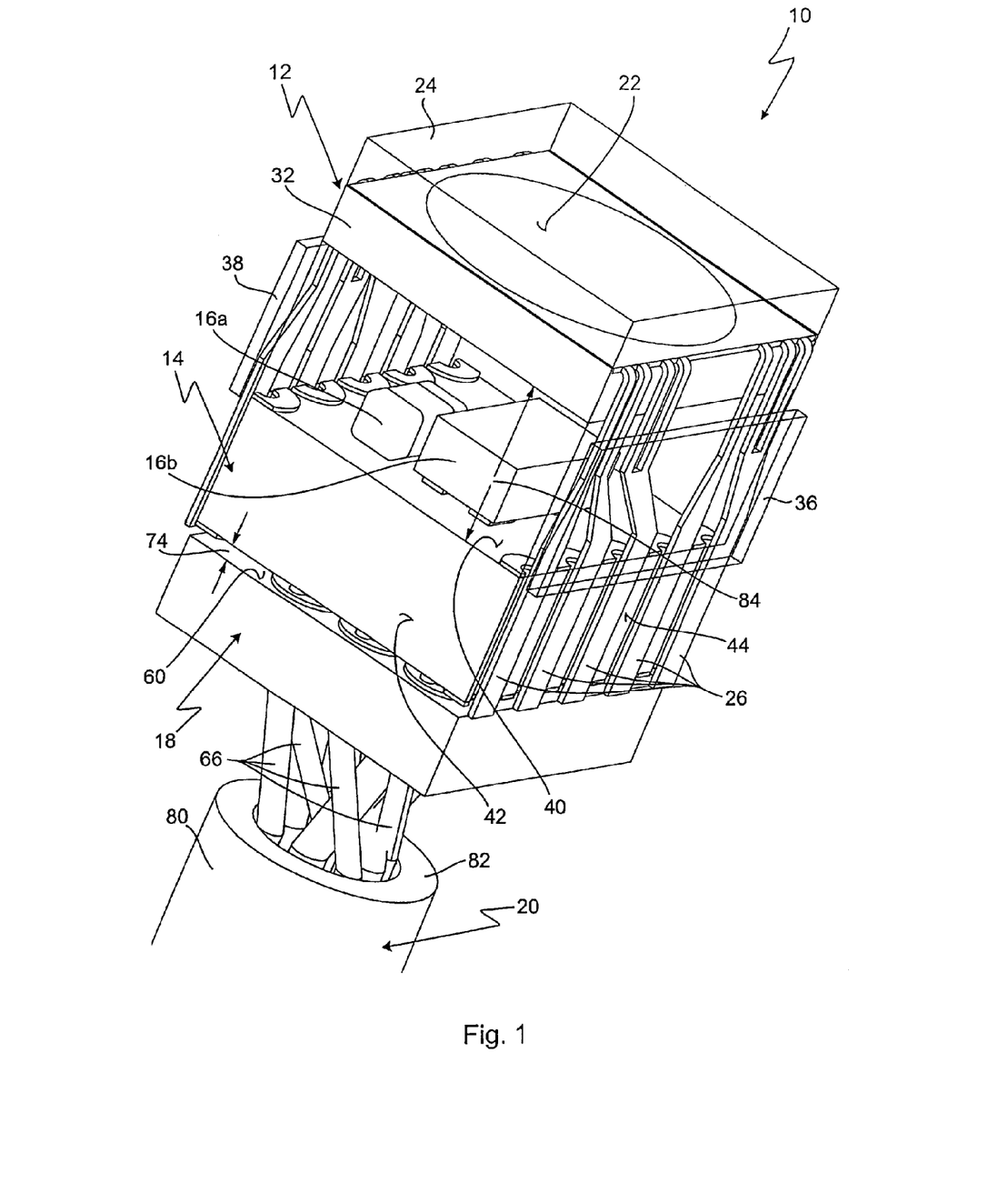
FIG. 1 shows an image pick-up module in an overall perspective view, the image pick-up module being represented greatly enlarged.
Figure 2:
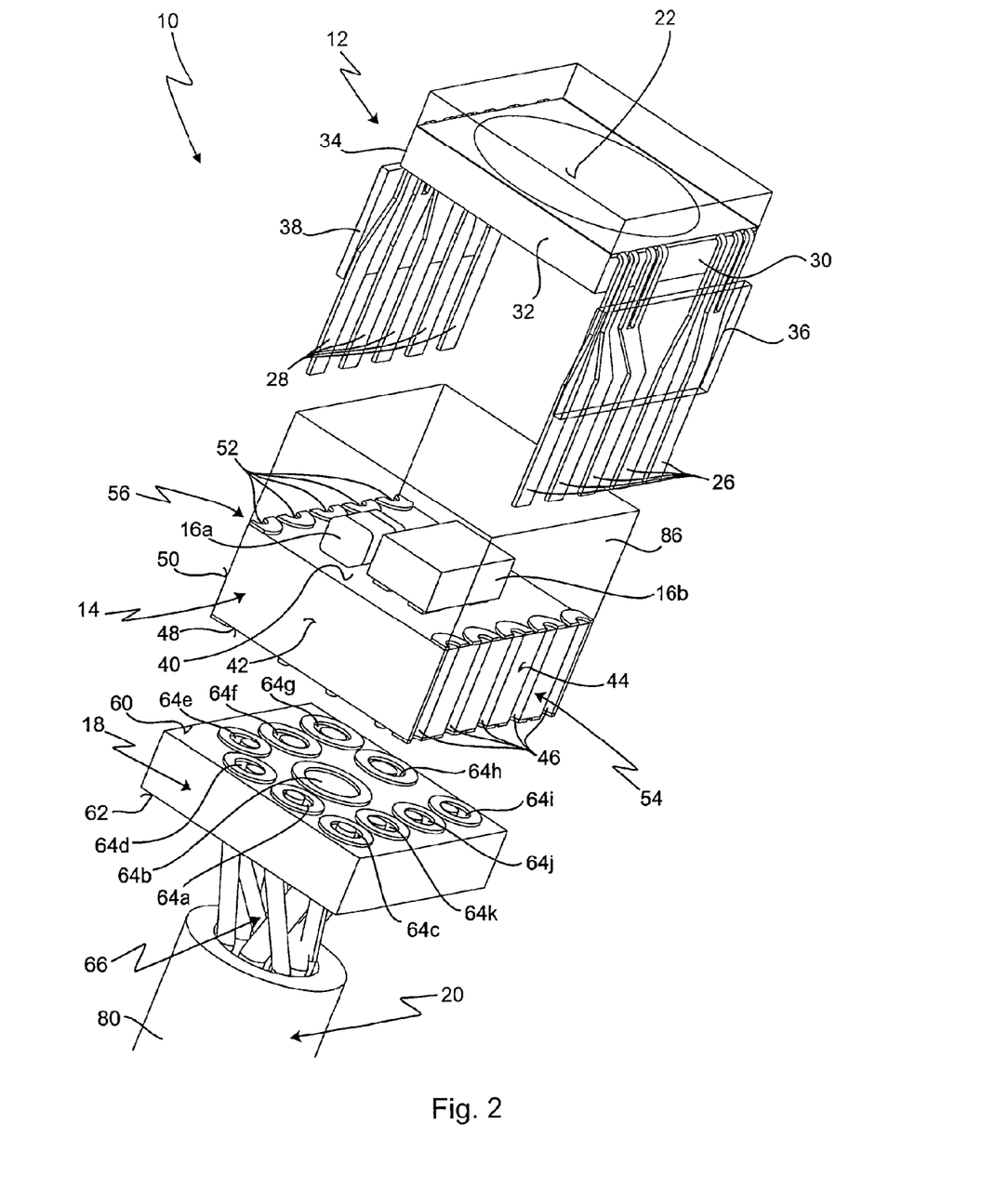
FIG. 2 shows a perspective exploded view of the image pick-up module in FIG. 1.
Figure 3:
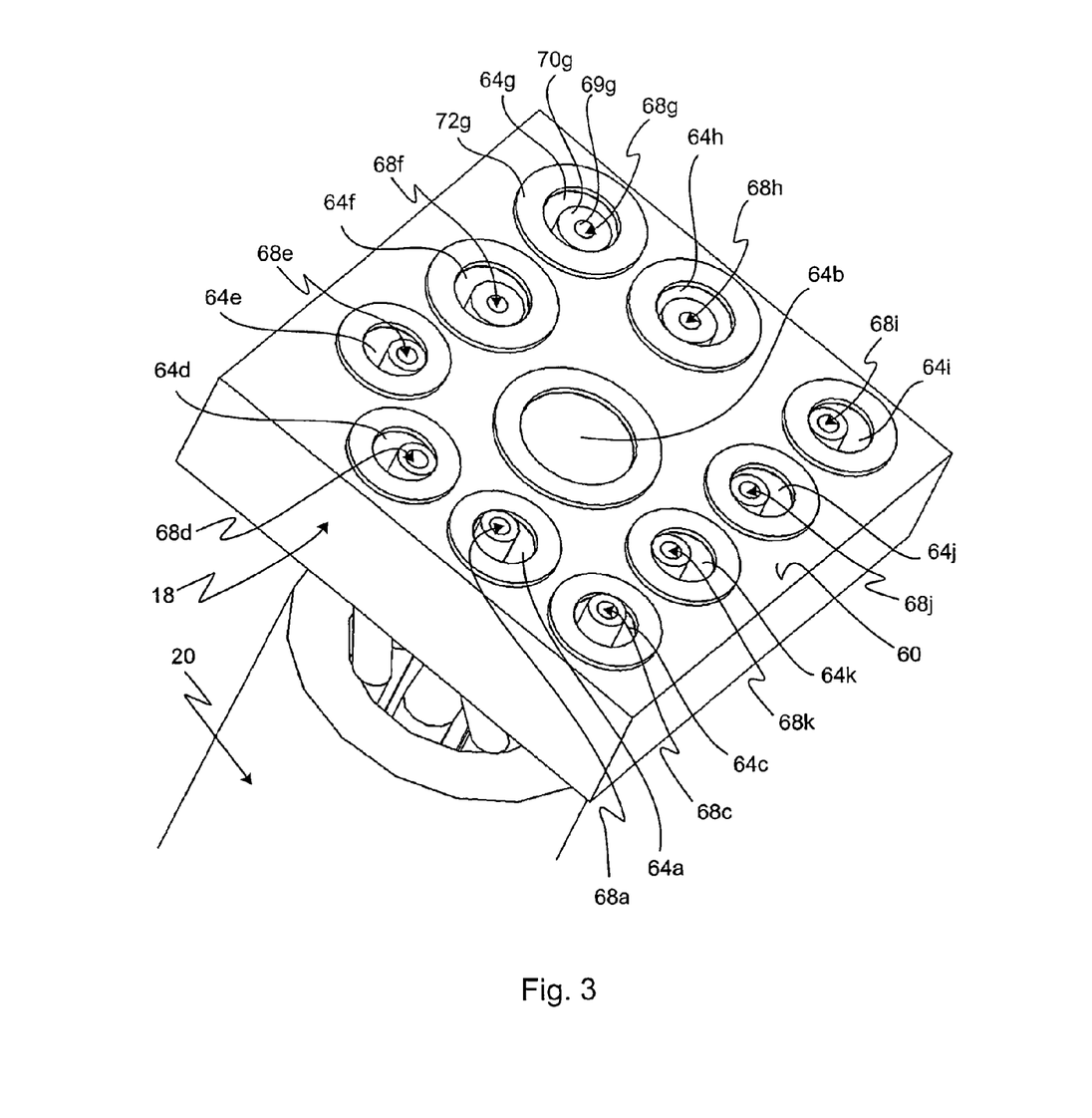
FIG. 3 shows a perspective view of a terminal circuit board of the image pick-up module in FIG. 1 with connected multi-wire cable.
Figure 4:
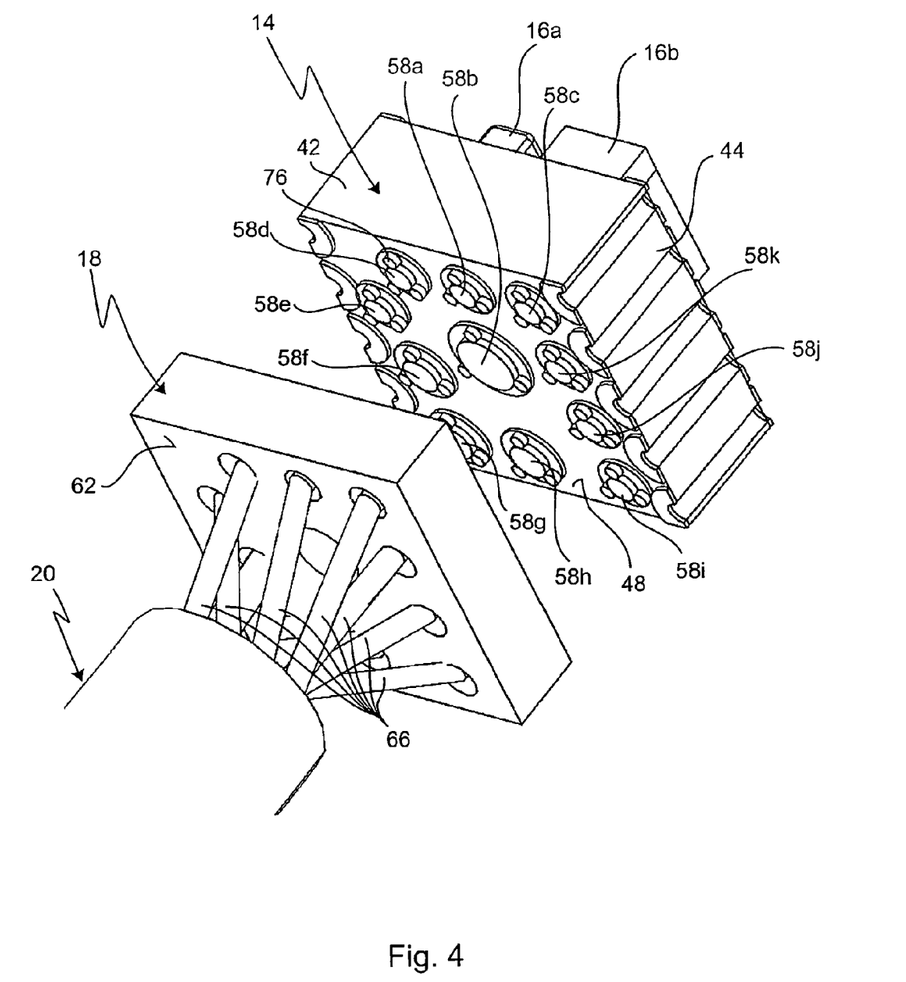
FIG. 4 shows a perspective view from below of the terminal circuit board in FIG. 3 and of a component circuit board of the image pick-up module in FIG. 1, the terminal circuit board and the component circuit board being shown in an exploded view.

FIG. 1 shows an image pick-up module, provided with the general reference symbol 10, in the assembled state. FIG. 2 shows the image pick-up module 10 in a representation in which the individual major assemblies of the image pick-up module 10 are shown in a partially exploded view. FIGS. 3 and 4 show further details of the image pick-up module 10.

The image pick-up module 10 can be installed, for example, into the distal tip of an endoscope or into a miniature medical camera, an exoscope, etc.

According to FIGS. 1 and 2, the image pick-up module 10 has as major assemblies an electronic image sensor 12, a first circuit board 14 which is also called component circuit board and is equipped with at least one electronic or electrical component 16a, 16b, two in the illustrative embodiment shown, a second circuit board 18 which is also called terminal circuit board, and a multi-wire cable 20.

The image pick-up module 10 is shown greatly enlarged in FIGS. 1 and 2. Naturally, the image pick-up module 10 is an opto-electronic component in miniaturized form.

In the description which follows, the individual major assemblies of the image pick-up module 10 are described.

The electronic image sensor 12 is constructed in CCD or CMOS technology in TAB configuration.

The image sensor 12 has a light-receiving surface 22 on which a cover glass 24 is attached. In use of the image pick-up module 10, light is incident on the light-receiving surface 22 through the transparent cover glass 24, the light signals received being converted into electrical signals in the image sensor 12. In the installed state of the image pick-up module 10, for example in an endoscope in its distal tip, the image pick-up module 10 is preceded by an objective in order to display an object to be observed on the light-receiving surface 22 of the image sensor 12.

The image sensor 12 has a plurality of contact fingers 26, 28. The contact fingers 26 are arranged in one row on one side 30 of a base body 32 of the image sensor 12 and the contact fingers 28 are arranged in one row on one side 34, which is opposite side 30, of the base body 32.

The contact fingers 26 and 28 extend perpendicularly to the light-receiving surface 22 of the image sensor 12 towards the first circuit board 14.

The contact fingers 26 which, in turn, are electrically conductive, are mechanically stabilized with respect to one another by an electrically non-conductive plate-shaped element 36. Similarly, the contact fingers 28 which, in turn, are electrically conductive, are mechanically stabilized relative to one another by an electrically non-conductive plate-shaped element 38.

The first circuit board 14, which is equipped with the electronic or electrical components 16a, 16b, has the shape of a flat cube overall. The first circuit board 14 has a surface 40 facing the image sensor 12, on which the electrical or electronic components 16a, 16b are arranged and brought into electrical contact. The surface 40 and thus also the first circuit board 14 overall are oriented in parallel with the light-receiving surface 22 of the image sensor 12 in the assembled state of the image pick-up module 10.

The first circuit board 14 also has four narrow sides, two of which can be seen in FIGS. 1 and 2, which are provided with the reference symbol 42 and 44.

The surface 40 of the circuit board 14 has, for example, an edge dimension of about 2 mm, whilst the height of the narrow sides 42 and 44, respectively, is about 1 mm or less in a direction perpendicular to the surface 40.

On the narrow side 44 of the first circuit board 14, an identical number of conductive indentations 46 is present in accordance with the number of contact fingers 26. The indentations are constructed as essentially half-cut-open cylinders, as can be seen, in particular, from FIG. 2. The indentations 46 extend from the surface 40 of the first circuit board 14 to an opposite surface 48 of the first circuit board 14 (see also FIG. 4). The conductivity of the indentations 46 is achieved by a corresponding metallization of the indentations 46, for example with gold. The half-cylindrical indentations 46 can be generated during the production of the first circuit board 14 in that the first circuit board 14 is initially produced with an excessive dimension in the direction of the narrow side 42 and through holes are then introduced into the edge area of the narrow side 44, and by cutting the circuit board 14 to measure, the cut being effected approximately centrally through the holes described above, the half-cylindrical indentations 46 are then created. In this process, the metallization of the indentations 46 can take place after the introduction of the holes or only after the holes have been cut open.

On a narrow side 50 opposite the narrow side 44, also conductive indentations 52 are formed in the form of essentially half-cut-open cylinders which extend going through from the surface 40 to the opposite surface 48.

The indentations 46 are used as contact points for bringing the contact fingers 26 into contact with the first circuit board 14. The indentations 52 are used as contact points 56 for bringing the contact fingers 28 of the image sensor 12 into contact with the first circuit board 14.

In the assembled state, shown in FIG. 1, of the image pick-up module 10, the contact fingers 26 are glued on or in the indentations 46, respectively, by means of a conductive adhesive and the contact fingers 28 are correspondingly glued on or in the indentations 52, respectively, in order to bring the contact fingers 28 conductively into contact with the first circuit board.

On the surface 48 facing away from the image sensor 12, the first circuit board 14 has a plurality of punctiform contact points which are provided with the reference symbols 58a to

58k. The contact points 58a to 58k exhibit no or, at the most, a minimum elevation from the surface 48 or in the μ range, respectively.

The first circuit board 14 is manufactured in a multi-layer structure, electrical lines extending correspondingly through the interior of the circuit board 14 so that the punctiform contact points 58a to 58k are electrically conductively connected partially to the conductive indentations 46 and 52 and partially to the electrical or electronic components 16a and 16b. The electrical components 16a and 16b are part of the control electronics of the image sensor 12.

The second circuit board 18, which is also called terminal circuit board, also has the form of a flat cube, the height of the second circuit board 18 in the direction perpendicular to the light-receiving surface 22 of the image sensor 12 being even less than the height of the first circuit board 14.

The second circuit board 18 is only used for terminating the cable 20.

The second circuit board 18 exhibits a surface 60 facing the first circuit board 14 and a surface 62 opposite it (see also FIG. 4). The surface 60 or the second circuit board 18, respectively, as such extends in the assembled state of the image pick-up module 10 in parallel with the light-receiving surface 22 of the image sensor 12 and in parallel with the circuit board 14.

The surface 60 of the second circuit board 18 is essentially level like the surface 48, facing the surface 60, of the first circuit board 14.

The second circuit board 18 exhibits a plurality of holes 64a to 64k which are in each case going through from the surface 62 to the opposite surface 60 of the second circuit board 18. The holes 64a to 64k are distributed over the second circuit board 18 between edges of the latter.

The surface distribution of the holes 64a to 64k in the second circuit board 18 then corresponds to the surface distribution of the contact points 58a to 58k on the surface 48 of the first circuit board 14. In other words, the occupancy of the surface 48 with the contact points 58a to 58k mirrors the occupancy of the circuit board 18 with the holes 64a to 64k.

Thus, one of the contact points 58a to 58k is allocated to each hole 64a to 64k immediately oppositely, i.e. contact point 58a is allocated to hole 64a, contact point 58b to hole 64b, contact point 58c to hole 64c, etc, immediately oppositely when the image pick-up module 10 is assembled.

The multi-wire cable 20 exhibits a plurality of wires 66.

The wires 66 are introduced into the holes 64a to 64k of the second circuit board 18, ends 68a to 68k of the wires 66 (the wire or wires 68b are not shown in the drawing but are present in the hole 64b in the same manner) ending at the surface 60 of the second circuit board 18, the ends 68a to 68k essentially being cut off bluntly flush with the surface 60 of the second circuit board 18.

The ends 68a to 68k of the wires 66 have wire jackets and wire cores exposed at the front end, as is shown for a wire core 69g and a wire jacket 70g of the end 68g of the corresponding wire in FIG. 3.

The edges of the holes 64a to 64k in the second circuit board 18 are covered with metallizations, for example gold rings as is shown for a gold ring 72g of the hole 64g in FIG. 3. Instead of the gold material, another metallization material can also be used or no such metallizations can also be provided.

The first circuit board 14 is electrically conductively brought into contact with the ends 68a to 68k of the wires 66 of the cable 20 via the punctiform contact points 58a to 58k, in a signal separately fashion.

Establishing the contact of the first circuit board 14 with the wires 66 of the cable 20 is effected by means of conductive joining points at the contact points 58a to 58k. Such joining points are preferably designed as adhesive or solder points. In this manner, the first circuit board 14 is not only electrically conductively brought into contact with the wires 66 of the cable 20, but the first circuit board 14 is also mechanically connected to the second circuit board 18 via the joining points.

As an alternative to the establishment of contact of the first circuit board 14 with the wires 66 of the cable 20 by means of conductive joining points, it can also be provided to provide a conductive rubber between the first circuit board 14 and the second circuit board 18, which conductive rubber is compressed locally in the area of each individual contact point 58a-58k and is electrically conductive due to the local compression between the respective contact point 58a-58k and the associated wire 66. In contrast, the conductive rubber remains insulating in a direction parallel to the planes of the circuit board 14 and the circuit board 18. When a conductive rubber is used, the first circuit board 14 is connected firmly to the second circuit board 18, for example by gluing together at, for example, the four corners at which the conductive rubber is not present or cut out for these purposes.

The aforementioned gold rings 72 are used for enlarging the contact points in order to ensure reliable contact between the contact points 58a to 58k and the wires 66 of the cable 20.

As can be seen from FIG. 1, the first circuit board 14 and the second circuit board 18 are spaced apart from one another only by a very thin gap 74, which can be in the μ range, in the assembled state of the image pick-up module 10. To adjust the gap 74 in a defined and reproducible manner during the assembling of the image pick-up module 10, spacers 76 (see FIG. 4) are arranged on the surface 48 of the circuit board 14, in this case at many or all of the contact points 58a to 58k. In the illustrative embodiment shown, three spacers 76 in the form of small so-called ball bonds are allocated to each of the contact points 58a to 58k. During the assembling of the image pick-up module 10, when the first circuit board 14 is placed onto the second circuit board 18 with the first contact points 58a to 58k, the spacers 76 prevent that the aforementioned adhesive or solder points are excessively compressed and thus smeared along the surface 48 of the first circuit board 14 and the surface 60 of the second circuit board 18, respectively, so that short circuits between individual contact points 58a to 58k are avoided and an establishment of contact, separated by signals, of the first circuit board 14 with the second circuit board 18 is ensured.

The individual wires 66 of the multi-wire cable 20 are furthermore fixed in the holes 64a to 64k by means of an adhesive which also creates a tension relief of the cable 20.

The cable 20 exhibits a cable jacket 80, the second circuit board 18 being brought as far as possible up to the cable root formed by the edge 82 of the cable jacket 80.

The image pick-up module 10 according to the invention has a very small axial constructional length in the direction perpendicular to the light-receiving surface 22 of the image sensor, which is desirable for installing the image pick-up module 10 into the distal tip of a flexible endoscope.

As can be seen from FIG. 1, the electrical or electronic components 16a, 16b are arranged on the surface 40 of the first circuit board 14 facing the image sensor 12. The image sensor 12 is spaced apart from the surface 40 by a distance 84, the space between the image sensor 12, or expressed more accurately its surface facing the surface 40, and the surface 40 being filled with a casting compound 86 (see FIG. 2), the casting compound 86 here being shown to be transparent to simplify the representation, but the casting compound, naturally, can also be non-transparent.

In the text which follows, an illustrative method for producing the image pick-up module 10 is described.

In a first step, the second circuit board 18 with the holes 64a to 64k located therein and the multi-wire cable 20 are provided.

In the next step, the cable jacket 80 of the cable 20 is taken off over a certain length which exposes the individual wires 66. The total shielding located on the inside of the cable jacket 80 is pulled backward. A further wire or strand is formed from the shieldings of the individual wires 66. All wires 66 (including the wires formed by the shieldings) are then introduced or threaded into the holes 64a to 64k in accordance with the wiring diagram until the ends 68a to 68k protrude from the surface 60 of the second circuit board 18. Naturally, it depends on the wiring diagram whether only one wire of the wires 66 is in each case introduced through one of the holes 64a to 64k, or optionally two or more of the wires 66 are also inserted.

The second circuit board 18 is pushed as far as possible towards the cable root (edge 82 of the cable jacket 80).

The ends 68a to 68k now protrude from the surface 60 of the second circuit board 18.

In the next step, the wires 66 are mechanically fixed in the holes 64a to 64k by means of an adhesive.

Apart from the wire cores 69 which are electrically conductive, the ends 68a to 68k of the wires 66 protruding from the surface 60 of the second circuit board 18 through the holes 64a to 64k also exhibit the wire jackets 70. Naturally, the aforementioned further wire which has been formed from the shieldings of the individual wires 66 does not exhibit a wire jacket.

In the next step, cutting is then effected by means of a suitable device in parallel with the surface 60 and perpendicularly to and through the protruding ends 68a to 68k of the wires 66, so that the ends 68a to 68k with their wire cores 69 and their wire jackets 70 essentially end flush with the surface 60 of the second circuit board 18. Trimming the individual cores 66 to the correct length can thus be performed in an automated manner by means of a robot, without first actually having to trim and strip the individual wires individually as in the known methods. Stripping the wires is completely superfluous.

The ends 68a to 68k of the wires 66 are now trimmed bluntly and the electrically conductive wire cores 69 are now exposed at the end faces and can be contacted.

In the next step, bonding points of a conductive adhesive are placed onto the ends 68a to 68k on the surface 60 of the second circuit board. This process, too, can be performed in an automated manner by means of a robot.

In the next step, the first circuit board 14, already previously equipped with the electrical or electronic components 16a, 16b, is placed onto the second circuit board 18 so that the first circuit board 14 is electrically conductively brought into contact with the ends 68a to 68k of the wires 66 via the contact points 58a to 58k. Placing the circuit board 14 onto the circuit board 18 can also be performed in an automated manner by means of a robot.

After the bonding points have cured, the first circuit board 14, the second circuit board 18 and the cable 20 are connected to one another separated by signals. After the bonding points have cured, the first circuit board 14 is also connected to the second circuit board 18 in a mechanically fixed manner.

It is now possible to test the functionality of all conductive connections of the assembled assembly of first circuit board 14, second circuit board 18 and cable 20 by measurement on the conductive indentations 46 and 52 of the first circuit board 14, and any poor parts can be eliminated, actually before the image sensor 12 is connected to the first circuit board 14.

In the next step, the image sensor 12 is taken out of its delivery package by means of laser light. In this state, the contact fingers 26 and 28 still extend in parallel with the light-receiving surface 22 of the image sensor 12. The contact fingers 26 and 28 are then bent over approximately perpendicularly to the light-receiving surface 22 of the image sensor 12.

Before this, the casting compound 86 has been applied in a predetermined thickness (related to the direction perpendicular to the light-receiving surface 22) onto the surface 40 of the first circuit board 14, and after the casting compound 86 has cured, the image sensor 12 is placed onto the casting compound 86. Due to the presence of the casting compound 86, the image sensor 12 assumes a reproducible, defined distance from the surface 40 of the first circuit board 14 when the base body 32 is placed onto the top surface of the casting compound 86, so that the contact fingers 26, 28 end in the correct length approximately at the level of the surface 48 of the circuit board 14.

In the last step, the contact fingers 26 and 28 are then glued to the conductive indentations 46 and 52, respectively, of the first circuit board 14 by means of a conductive adhesive. The image sensor 12 is now electrically conductively brought into contact with the first circuit board 14.

The image pick-up module 10 is now completed.

From the above text it can be seen that all the aforementioned method steps of assembling the image pick-up module 10 can be performed in an automated manner and preferably by means of a robot.

What is claimed is:

1. An image pick-up module, comprising:
   an electronic image sensor which has a plurality of contact fingers which are arranged in at least one row, the electronic image sensor having a light receiving surface,
   a first circuit board being arranged in parallel with the light-receiving surface of the image sensor, the first circuit board having
     at least one electronic or electrical component,
     a first surface facing from the image sensor,
   a second circuit board arranged in parallel with the first circuit board on a side of the first circuit board facing away from the image sensor, the second circuit board having
     a second surface facing from the first circuit board, and
     a third surface facing the first circuit board, the third surface being essentially level overall,
     a plurality of holes distributed two-dimensionally over the second circuit board between edges of the second circuit board, the holes going through from the second surface to the third surface of the second circuit board, the holes being distributed according to a first distribution,
   a cable having a plurality of wires being connected to the second circuit board and leading away from the second surface of the second circuit board, the wires having ends introduced into the holes of the second circuit board, and the ends of the wires being located approximately on the third surface of the second circuit board,
   the first circuit board has on the first surface facing the second circuit board a plurality of punctiform first electrical contact points distributed according to a second distribution which corresponds to the first distribution of the ends of the wires on the third surface of the second circuit board, the first circuit board being in electrically conductive contact with the ends of the wires via the first electrical contact points; and, wherein the first circuit board has, on at least one narrow side perpendicular to the first surface, a plurality of second contact points, the contact fingers of the image sensor being in electrically conductive contact at the second contact points.

2. The image pick-up module of claim 1, wherein the second contact points are conductive indentations, extending in the direction from a fourth surface of the first circuit board facing the image sensor to the first surface of the first circuit board, on the at least one narrow side.

3. The image pick-up module of claim 2, wherein the conductive indentations are configured as essentially half-cut-open cylinders.

4. The image pick-up module of claim 1, wherein the first circuit board is in contact with and connected to the wires at the first contact points by conductive joining points.

5. The image pick-up module of claim 1, wherein, between the first circuit board and the second circuit board in the area of the first contact points, a two dimensional element is arranged which is manufactured from an insulating compressible material which is interspersed with conductive particles, the two dimensional element being locally compressed at the first contact points in order to bring the first circuit board electrically conductively into contact with the wires.

6. The image pick-up module of claim 1, wherein, on the first surface of the first circuit board, spacers are present which define a narrow gap between the first surface of the first circuit board and the third surface of the second circuit board.

7. The image pick-up module of claim 1, wherein the wires are fixed in the holes of the second circuit board by means of adhesive.

8. The image pick-up module of claim 1, wherein the ends of the wires have wire cores and wire jackets, the wire cores and the wire jackets end approximately tlush with the edges of the holes on the third surface of the second circuit board.

9. An image pick-up module, comprising:
an electronic image sensor which has a plurality of contact fingers which are arranged in at least one row, the electronic image sensor having a light receiving surface,
a first circuit board being arranged in parallel with the light-receiving surface of the image sensor, the first circuit board having
at least one electronic or electrical component,
a first surface facing away from the image sensor,
a second circuit board arranged in parallel with the first circuit board on a side of the first circuit board facing away from the image sensor, the second circuit board having
a second surface facing away from the first circuit board, and a third surface facing the first circuit board, the third surface being essentially level overall,
a plurality of holes distributed two-dimensionally over the second circuit board between edges of the second circuit board, the holes going through from the second surface to the third surface of the second circuit board, the holes being distributed according to a first distribution,
a cable having a plurality of wires being connected to the second circuit board and leading away from the second surface of the second circuit board, the wires having ends introduced into the holes of the second circuit board, and the ends of the wires being located approximately on the third surface of the second circuit board, the first circuit board has on the first surface facing the second circuit board a plurality of punctiform first electrical contact points distributed according to a second distribution which corresponds to the first distribution of the ends of the wires on the third surface of the second circuit board the first circuit board being in electrically conductive contact with the ends of the wires via the first electrical contact points; and, wherein the image sensor is spaced apart from the first circuit board, a space between the image sensor and the circuit board being filled with a casting compound.

10. A method for producing an image pick-up module, comprising:
providing an electronic image sensor which having a plurality of contact fingers arranged in at least one row,
providing a first circuit board having first surface and at east one electronic or electrical component, the first circuit board further having a plurality of punctiform first electrical contact points on the first surface, the first contact points being two-dimensionally distributed according to a first distribution,
providing a second circuit board having second surface being essentially level overall and, further, having a plurality of through holes two-dimensionally distributed over the second circuit board between edges of the second circuit board according to a second distribution corresponding to the first distribution,
providing a cable having a plurality of wires having ends,
introducing the ends of the wires of the cable into the holes of the second circuit board,
arranging the ends of the wires approximately in the area of the second surface of the second circuit board,
bringing the first contact points of the first circuit board electrically conductively into contact with the ends of the wires; and,
applying a casting compound onto the first circuit board, wherein the image sensor is placed onto the casting compound and the contact fingers of the image sensor are brought into contact with the first circuit board at second contact points which are arranged on at least one narrow side of the first circuit board.

11. The method of claim 10, wherein the wires have wire jackets, further comprising introducing the ends of the wires into the holes with their wire jackets until the wires with their wire jackets protrude from the holes, fixing the wires in the holes, and effecting cutting along the second surface of the second circuit board perpendicularly to and through the wires, so that the ends of the wires end approximately flush with edges of the holes on the second surface of the second circuit board.

12. The method of claim 10, further comprising applying conductive joining points onto at least one of the following: the ends of the wires, the first contact points, and placing the first contact points of the first circuit board onto the joining points in order to bring the first circuit board into contact with the wires.

13. The method of claim 10, further comprising providing a two-dimensional element manufactured from an insulating compressible material which is partially interspersed with conductive particles, arranging the two dimensional element on the second circuit board in the area of the ends of the wires, pressing the first circuit board with the first contact points onto the two-dimensional element, and fixing the first circuit board on the second circuit board.

14. The method of claim 10, further comprising testing the functionality of conductive connections of the first and second circuit board, before applying the casting compound and before placing the image sensor at the second contact points.

* * * * *